United States Patent
Fang et al.

(10) Patent No.: US 8,846,575 B2
(45) Date of Patent: *Sep. 30, 2014

(54) HIGH-THROUGHPUT HIGH-INFORMATION CONTENT LABEL-FREE CELL BIOLOGY SCREENING METHODS

(75) Inventors: Ye Fang, Painted Post, NY (US); Anthony Glenn Frutos, Painted Post, NY (US); David H Randle, Corning, NY (US); Elizabeth Tran, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 964 days.

This patent is subject to a terminal disclaimer.

(21) Appl. No.: 12/569,407

(22) Filed: Sep. 29, 2009

(65) Prior Publication Data

US 2010/0087332 A1 Apr. 8, 2010

Related U.S. Application Data (63) Continuation-in-part of application No. 12/388,685, filed on Feb. 19, 2009, now Pat. No. 8,313,898.

(60) Provisional application No. 61/068,266, filed on Mar. 5, 2008, provisional application No. 61/182,516, filed on May 29, 2009.

(51) Int. Cl.
| | |
|---|---|
| *C40B 30/04* | (2006.01) |
| *G01N 33/74* | (2006.01) |
| *C12Q 1/02* | (2006.01) |
| *G01N 33/543* | (2006.01) |
| *G01N 33/50* | (2006.01) |

(52) U.S. Cl.
CPC .............. *C12Q 1/025* (2013.01); *G01N 33/74* (2013.01); *G01N 2333/71* (2013.01); *G01N 33/54373* (2013.01); *G01N 2333/726* (2013.01); *G01N 33/5008* (2013.01); *G01N 2500/10* (2013.01)
USPC ............................................................ 506/9

(58) Field of Classification Search
None
See application file for complete search history.

(56) References Cited

U.S. PATENT DOCUMENTS

| 4,815,843 A | 3/1989 | Tiefenthaler et al. ......... 356/128 |
| 5,305,074 A | 4/1994 | Feldman ...................... 356/345 |

(Continued)

FOREIGN PATENT DOCUMENTS

| WO | WO 2005/005979 | 1/2005 |
| WO | WO 2005/017507 | 2/2005 |

(Continued)

OTHER PUBLICATIONS

Cunningham et al. (Sep. 2004) Journal of Biomolecular Screening vol. 9 pp. 481 to 490.*

(Continued)

*Primary Examiner* — Christian Boesen
(74) *Attorney, Agent, or Firm* — John L. Haack (57) ABSTRACT

A method for hit compound identification in a high throughput, label-free biosensor cellular assay, one method including, for example:
generating at least one pathway-specific kinetic profile for a target receptor;
generating a relational table that integrates each kinetic profile;
determining a delta response with the relational table for candidate compounds screened against the target receptor; and
identifying one or more hit compounds based upon the separation of the delta response from a threshold.

12 Claims, 3 Drawing Sheets

(56) References Cited

U.S. PATENT DOCUMENTS

| | | | |
|---|---|---|---|
| 5,738,825 A | 4/1998 | Rudigier et al. | 422/82.11 |
| 6,233,471 B1 | 5/2001 | Berner et al. | 600/345 |
| 6,707,561 B1 | 3/2004 | Budach et al. | 356/521 |
| 6,727,071 B1 | 4/2004 | Dunlay et al. | 435/7.21 |
| 6,867,869 B2 | 3/2005 | Budach et al. | 356/521 |
| 6,870,630 B2 | 3/2005 | Budach et al. | 356/521 |
| 6,893,705 B2 | 5/2005 | Thomas et al. | 428/141 |
| 6,985,664 B2 | 1/2006 | Caracci et al. | 385/130 |
| 7,064,844 B2 | 6/2006 | Budach et al. | 356/521 |
| 7,105,347 B2 | 9/2006 | Fang et al. | 435/455 |
| 7,264,973 B2 | 9/2007 | Lin et al. | 436/518 |
| 7,286,221 B2 | 10/2007 | Caracci et al. | 356/300 |
| 7,627,201 B2 | 12/2009 | Tiefenthaler | 385/12 |
| 2002/0127565 A1 | 9/2002 | Cunningham et al. | 435/6 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0091397 A1 | 5/2004 | Picard | 422/99 |
| 2004/0132172 A1 | 7/2004 | Cunningham et al. | 435/287.2 |
| 2004/0151626 A1 | 8/2004 | Cunningham et al. | 422/58 |
| 2004/0223881 A1 | 11/2004 | Cunningham et al. | 422/82.05 |
| 2004/0235198 A1 | 11/2004 | Marx et al. | 436/527 |
| 2004/0263841 A1 | 12/2004 | Caracci et al. | 356/300 |
| 2005/0070027 A1 | 3/2005 | Gollier et al. | 436/518 |
| 2005/0100904 A1 | 5/2005 | Yoshizato et al. | 435/6 |
| 2005/0158880 A1 | 7/2005 | Ostuni et al. | 438/1 |
| 2005/0236554 A1 | 10/2005 | Fontaine et al. | 250/208.1 |
| 2006/0063276 A1 | 3/2006 | Jiang et al. | 436/518 |
| 2006/0205058 A1 | 9/2006 | Frutos et al. | 435/287.1 |
| 2006/0205092 A1 | 9/2006 | Lackritz et al. | 436/525 |
| 2006/0223051 A1 | 10/2006 | Fang et al. | 435/4 |

FOREIGN PATENT DOCUMENTS

| | | | |
|---|---|---|---|
| WO | WO2006/086883 | 8/2006 | C12Q 1/66 |
| WO | WO2006/107506 | 10/2006 | G01N 33/543 |
| WO | WO 2006/107967 | 10/2006 | |
| WO | WO 2006/108183 | 10/2006 | |
| WO | WO2007/011959 | 1/2007 | C12Q 1/00 |
| WO | WO 2007/015878 | 2/2007 | |
| WO | WO 2007/018872 | 2/2007 | |
| WO | WO2008/156560 | 12/2008 | G01N 21/47 |

OTHER PUBLICATIONS

B. January et al., "$\beta_2$-Adrenergic Receptor Desensitization, Internationalization, and Phosphorylation in Response to Full and Partial Agonists", *The Journal of Biological Chemistry*, vol. 272, No. 38, pp. 23871-23879.

Jordan et al., "Surface Plasmon Resonance Imaging Measurements of Electrostatic Biopolymer Adsorption Onto Chemically Modified Gold Surfaces", *Anal. Chem.*, 1997, vol. 69, pp. 1449-1456.

Hug, T. S., et al., "Optical waveguide lightmode spectroscopy as a new method to study adhesion of anchorage-dependent cells as an indicator of metabolic state", Biosensors & Bioelectronics 16 (2001), p. 865-874.

Li, S-Y., "Measurement of Adhesion and Spreading Kinetics of Baby Hamster Kidney and Hybridoma Cells Using an Integrated Optical Method", Biotechnol. Prog. 1994, 10, p. 520-524.

Ramsden, J. J., "Optical Method for Measurement of Number and Shape of Attached Cells in Real Time", Cytometry 19, 1995, p. 97-102.

Hug, T. S., "Optical Waveguide Lightmode Spectroscopy (OWLS) to Monitor Cell Proliferation Quantitatively", Biotechnology and Bioengineering, vol. 80, No. 2, Oct. 20, 2002, p. 213-221.

Horvath, R., "Optical waveguide sensor for on-line monitoring of bacteria", Optics Letters, Jul. 15, 2003, vol. 28, No. 14, p. 1233-1235.

Hug, T. S., "Biophysical Methods for Monitoring Cell-Substrate Interactions in Drug Discovery", ASSAY and Drug Development Technologies, vol. 1, No. 3, 2003, p. 479-488.

Horvath, R., "Monitoring of living cell attachment and spreading using reverse symmetry waveguide sensing", Applied Physics Letters 86, (2005), 071101-1-071101-3.

Corso, C. D., "An investigation of antibody immobilization methods employing organosilanes on planar ZnO surfaces for biosensor applications", Biosensors and Bioelectronics 24, (2008), p. 805-811.

Beske Oren et al, "A novel encoded particle technology that enables simultaneous interrogation of multiple cell types", Journal of Biomolecular Screening: The official Journal of the Society for Biomolecular Screening, vol. 9, No. 3, Apr. 2004, pp. 173-185.

Ye Fang et al, "Label-free cell-based assays for GPCR screening", Combinatorial Chemistry & High Throughput Screening, vol. 11, No. 5, Jun. 2008, pp. 357-369.

M. Azzi et al., "β-Arrestin-mediated activation of MAPK by inverse agonists reveals distinct active conformations for G protein-coupled receptors", *PNAS*, Sep. 30, 2003, vol. 100, No. 20, pp. 11406-11411.

J.G. Baker et al., "Influence of Agonist Efficacy and Receptor Phosphorylation on Antagonsit Affinity Measurements: Differences between Second Messenger and Reporter Gene Responses", *Mol. Pharmacol.*, 2003, vol. 64, No. 3, pp. 679-688.

Brecht et al., "Optical Probes and Transducers*", *Biosensors and Bioelectronics*, vol. 10, 1995, pp. 923-936.

K. Choudhuri et al., "T-cell receptor triggering is critically dependent on the dimensions of its peptide-MHC ligand", *Nature*, vol. 436, Jul. 28, 2005, pp. 578-582.

Clerc et al., "Direct Immunosensing With an Integrated-Optical Output Grating Coupler", Sensors & Actuators B, vol. 40, 1997, pp. 53-58.

Drews, "Drug Discovery: A Historical Perspective", *Science*, Mar. 17, 2000, vol. 287, pp. 1960-1964.

G.L. Duveneck et al., "Novel Bioaffinity Sensors for Trace Analysis Based on Luminescence Excitation by Planar Waveguides", *Sensors and Actuators B*, vol. 38-39, 1997, pp. 88-95.

G.L. Duveneck et al., "Review on Fluorescence-Based Planar Waveguide Biosensors", *Proc. SPIE*, vol. 3858, 1999, pp. 59-71.

G.L. Duveneck et al., "Two-Photon Fluorescence Excitation of Macroscopic Areas on Planar Waveguides", *Biosensors and Bioelectronics*, vol. 18, 2003, pp. 503-510.

Ye Fang et al., "Cellular functions of cholesterol probed with optical biosensors", *Biochimica et Biophysica Acta*, vol. 1763, 2006, pp. 254-261.

Y. Fang et al., "Characteristics of Dynamic Mass Redistribution of Epidermal Growth Factor Receptor Signaling in Living Cells Measured with Label-Free Optical Biosensors", *Anal. Chem.*, vol. 77, 2005, pp. 5720-5725.

Y. Fang et al., "G-Protein-Coupled Receptor Microarrays", *ChemBioChem*, Oct. 4, 2002, vol. 3, No. 10, pp. 987-991.

Y. Fang, "Label-Free Cell-Based Assays with Optical Biosensors in Drug Discovery", *Assay and Drug Development Technologies*, vol. 4, No. 5, 2006, pp. 583-595.

Y. Fang et al., "Non-Invasive Optical Biosensor for Assaying Endogenous G Protein-Coupled Receptors in Adherent Cells", *Journal of Pharmacological and Toxicological Method*, vol. 55, 2007, pp. 314-322.

Y. Fang et al., "Optical biosensor differentiates signalling of endogenous $PAR_1$ and $PAR_2$ in A431 cells", *BMC Cell Biology*, 2007, vol. 8, No. 24, pp. 1-12, http://www.biomedcentral.com/1471-2121/8/24.

Ye Fang et al., "Optical Biosensor Provides Insights for Bradykinin B2 Receptor Signaling in A431 Cells", *FEBS Letters*, vol. 579, 2005, pp. 6365-6374.

Y. Fang et al., "Probing cytoskeleton modulation by optical biosensors", *FEBS Letters*, vol. 579, 2005, pp. 4175-4180.

Y. Fang et al., "Resonant Waveguide Grating Biosensor for Living Cell Sensing", *Biophysical Journal*, vol. 91, Sep. 2006, pp. 1925-1940.

(56) References Cited

OTHER PUBLICATIONS

I. Giaever et al., "Monitoring fibroblast behaviour in tissue culture with an applied electric field", *Proc. Natl. Acad. Sci.*, Jun. 1984, vol. 81, pp. 3761-3764.
H.M. Grandin et al., "Waveguide Excitation Fluorescence Microscopy: A New Tool for Sensing and Imaging the Biointerface", *Biosensors and Bioelectronics*, vol. 21, 2006, pp. 1476-1482.
A. Grakoui et al., "The Immunological Synapse: A Molecular Machine Controlling T Cell Activation", *Science*, vol. 285, Jul. 9, 1999, pp. 221-227.
M. Hide et al., "Real-Time Analysis of Ligand-Induced Cell Surface and Intracellular Reactions of Living Mast Cells Using a Surface Plasmon Resonance-Based Biosensor", *Analytical Biochemistry*, vol. 302, 2002, pp. 28-37.
Morhard et al., "Immobilization of Antibodies in Micropatterns for Cell Detection by Optical Diffraction", *Sensors and Actuators B*, vol. 70, 2000, pp. 232-242.
K. Mossman et al., "Micropatterned supported membranes as tools for quantitative studies of the immunological synapse", *Chemical Society Reviews*, vol. 36, 2007, pp. 46-54.
P.M. Nellen et al., "Integrated Optical Input Grating Couplers as Biochemical Sensors", *Sensors and Actuators*, 1988, vol. 15, pp. 285-295.
Pierce et al., "Seven-Transmembrane Receptors", *Nature Reviews, Molecular Cell Biology*, vol. 3, Sep. 2002, pp. 639-650.
Ramsden et al., "Kinetics of Adhesion and Spreading of Animal Cells", *Biotechnology and Bioengineering*, vol. 43, 1994, pp. 939-945.
M.D. Salik et al., Resonant Excitation Analysis of Waveguide Grating Couplers, *Optics Communications*, vol. 193, Jun. 15, 2001, pp. 127-131.
M.A. Simmons, "Functional Selectivity, Ligand-Directed Trafficking, Conformation-Specific Agonism: What's in a Name?", *Molecular Interventions*, Jun. 2005, vol. 5, Issue 3, pp. 154-157.
E.A. Smith et al., "Surface Plasmon Resonance Imaging as a Tool to Monitor Biomolecular Interactions in an Array Based Format", *Applied Spectroscopy*, 2003, vol. 57, No. 11, pp. 320A-332A.
K. Solly et al., "Application of Real-Time Cell Electronic Sensing (RT-CES) Technology to Cell-Based Assays", *ASSAY and Drug Development Technologies*, 2004, vol. 2, No. 4, pp. 363-372.
Tiefenthaler et al., "Integrated Optical Switches and Gas Sensors", *Optics Letters*, Apr. 1984, vol. 10, No. 4, pp. 137-139.
E. Verdonk et al., "Cellular Dielectric Spectroscopy: A Label-Free Comprehensive Platform for Functional Evaluation of Endogenous Receptors", *ASSAY and Drug Development Technologies*, 2006, vol. 4, No. 5, pp. 609-619.
G. Voirin et al., "$Si_3N_4/SiO_2/Si$ Waveguide Grating for Fluorescent Biosensors", *Proc. SPIE*, vol. 3620, 1999, pp. 109-116.
J. Vörös et al., "Optical Grating Coupler Biosensors", *Biomaterials*, vol. 23, 2002, pp. 3699-3710.
Z.H. Wang et al., "A Label-Free Multisensing Immunosensor Based on Imaging Ellipsometry", *Anal. Chem.*, 2003, vol. 75, pp. 6119-6123.
L.C. Waters et al., "Microchip Device for Cell Lysis, Multiplex PCR Amplification, and Electrophoretic Sizing", *Anal. Chem.*, 1998, vol. 70, pp. 158-162.
P.N. Zeller et al., "Single-Pad Scheme for Integrated Optical Fluorescence Sensing", *Biosensors & Bioelectronics*, vol. 15, 2000, pp. 591-595.
W.R. Holland et al., "Waveguide Mode Enhancement of Molecular Fluorescence", *Optics Letters*, vol. 10, No. 8, Aug. 1985, pp. 414-416.
B. Jan. et al., "$\beta_2$-Adrenergic Receptor Desensitization, Internationalization, and Phosphorxlation in Response to Full and Partial Agonists", *The Journal of Biological Chemistry*, vol. 272, No. 38, pp. 23871-23879, 1997.
Jin et al., "A Biosensor Concept Based on Imaging Ellipsometry for Visualization of Biomolecular Interactions", *Analytical Biochemistry*, vol. 232, 1995, pp. 69-72.
C.E. Jordan et al., "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.
Jodan et al., "Surface Plasmon Resonance Imaging Measurements of electrostatic Biopolymer Adsorption Onto Chemically Modified Gold Surfaces", *Anal. Chem.*, 1997, vol. 69, pp. 1449-1456.
P. Lalanne et al., "Highly Improved Convergence of the Coupled-Wave Method for TM Polarization", *J. Opt. Soc. Am. A*, vol. 13, No. 4, Apr. 1996, pp. 779-784.
G. Liapakis et al., "Synergistic Contributions of the Functional Groups of Epinephrine to Its Affinity and Efficacy at the $\beta_2$ Adrenergic Receptor", *Mol. Pharmacol.*, 2004, vol. 65, No. 5, pp. 1181-1190.
Z. Lu et al., "Epidermal Growth Factor-Induced Tumor Cell Invasion and Metastasis Initiated by Dephosphorylation and Downregulation of Focal Adhesion Kinase", *Molecular and Cellular Biology*, Jun. 2001, vol. 21, No. 12, pp. 4016-4031.
L. Lorenzelli, et al., "Bioelectrochemical signal monitoring of in-vitro cultured cells by means of an automated microsystem based on solid state sensor-array", *Biosensors and Bioelectronics*, 2003, vol. 18, pp. 621-626.
Ma et al., "From the Analyst's Couch: Value of Novelty?", *Nature Reviews, Drug Discovery*, vol. 1, Aug. 2002, pp. 571-572.
Tran et al., "Duplexed Label-Free G Protein-Coupled Receptor Assays for High-Throughput Screening", *Journal of Biomolecular Screening* 13(10); 2008; 2008 Society for Biomolecular Sciences, pp. 975-985.
Signal Pathway Identification and Deconvolution, www.cellkey.com/apps2.html, Accessed on Dec. 19, 2008.
S.A. Green et al., "Sustained Activation of a G Protein-coupled Receptor via "Anchored" Agonist Binding", *The Journal of Biological Chemistry*, vol. 271, No. 39, 1996, pp. 24029-24035.
B. Jan. et al., "$\beta_2$-Adrenergic Receptor Desensitization, Internationalization, and Phosphorylation in Response to Full and Partial Agonists", *The Journal of Biological Chemistry*, vol. 272, No. 38, 1997, pp. 23871-23879.
G. Liapakis et al., "The Forgotten Serine", *The Journal of Biological Chemistry*, vol. 275, No. 48, 2000, pp. 37779-37788.
G. Swaminath et al., "Probing the $\beta_2$ Adrenoceptor Binding Site with Catechol Reveals Differences in Binding and Activation by Agonists and Partial Agonists", *The Journal of Biological Chemistry*, vol. 280, No. 23, 2005, pp. 22165-22171.
J.D. Urban et al., "Functional Selectivity and Classical Concepts of Quantitative Pharmacology", *The Journal of Pharmacology and Experimental Therapeutics*, vol. 320, No. 1, 2007, pp. 1-13.
Zeptosens—Bioanalytical Solutions, http://www.zeptosens.com/en/, Accessed on Dec. 19, 2008.

* cited by examiner

HIGH-THROUGHPUT HIGH-INFORMATION CONTENT LABEL-FREE CELL BIOLOGY SCREENING METHODS

CLAIMING BENEFIT OF PRIOR FILED U.S. APPLICATION

This application, first filed on May 29, 2009, as U.S. Provisional Application No. 61/182,516, is a continuation-in-part and claims the benefit of U.S. patent application Ser. No. 12/388,685, filed on Feb. 19, 2009 now U.S. Pat. No. 8,313,898 which claims the benefit of U.S. Provisional Application No. 61/068,266, filed on Mar. 5, 2008. The entire disclosure of any publications, patents, and patent documents mentioned herein is incorporated by reference.

BACKGROUND

The disclosure generally relates to a method for identifying a hit compound, for example, in a label-free cellular assay, or like applications.

SUMMARY

The disclosure provides a method for identifying a hit compound, for example, in a label-free, cellular assay. The disclosed method provides high-throughput and high-information content screen capability and can include details of signal pathway interaction, such as activation.

BRIEF DESCRIPTION OF THE DRAWING(S)

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

In embodiments, the disclosure provides a method that combines pathway high-information content screening with the high-throughput capability of HTS. The method can be generally accomplished, for example, with the Corning® Epic® System (machine), and like label-free platforms. In embodiments, the disclosed method provides a method and a machine implementation including an algorithm, which method can simultaneously identify compound hits and the molecular pathways that the hit compound activates, or otherwise influence, in label-free high-throughput cellular assays (physical transformation).

Identification of compound hits in a recognized cellular assay can be accomplished, for example, using assay systems having a single numerical read-out, such as high-throughput screening (HTS). In HTS, each response is compared to a threshold value based upon control compounds. All compounds which exceed that threshold are designated as hits for further investigation. This approach enables large numbers of compounds to be rapidly tested but typically can only provide information about a single biological pathway. Alternatively, compounds can be screened in an assay that permits the simultaneous study of multiple biological pathways using automated cellular imaging systems, such as high-information content screening (HICS). Using HICS, compounds can be classified according to different biological criteria. However, the requirement for continuous data acquisition and analysis can reduce the overall throughput of the assay (see for example, Hertberg, R. P., et al., "High-throughput screening: new technology for the 21st century," *Curr. Opin. Chem. Biol.*, 2000, 4, 445-451; Macarron, R., "Critical review of the role of HTS in drug discovery," *Drug Discov Today,* 2006, 11, 277-279, and Rausch, O., "High content cellular screening," *Curr Opin Chem Biol,* 2006, 10, 316-320).

Label-free detection platforms have been used to demonstrate that specific signaling pathways can have unique response profiles, which profiles appear to be universal across multiple cell lines that have been evaluated. In particular, G-protein-coupled receptors (GPCRs) (seven-transmembrane protein) activate signaling mechanisms that can be readily classified according to characteristic kinetic responses (see Verdonk, E., et al., "Cellular Dielectric Spectroscopy: A Label-Free Comprehensive Platform for Functional Evaluation of Endogenous Receptors," *Assay Drug Dev Technol,* 2006, 4, 609-619; and Fang, Y., et al., "Non-invasive optical biosensor for assaying endogenous G protein-coupled receptors in adherent cells," *J Pharmacol Toxicol Methods,* 2007, 55, 314-322). Patent documents which mention label-free sensing systems and applications, such as for identifying compounds, include, for example, WO2008156560 (SRU), WO2007011959 (Quintessence Biosciences, Inc.) and WO2006108183 (Corning, Inc.). Typically, these response profiles are generated by continuous measurement for time periods up to about 1 hour, which durations can foreclose the use of this approach for HTS. However, the essence of the profile, such as general shape contours and the approximate and relative magnitudes, can be captured with a small subset of the data points gathered over the duration of the response. In embodiments of the disclosure, label-free systems can permit acquisition of high-information content with little or no reduction in overall throughput.

In embodiments, the disclosure provides a number of advantages as discussed below. The method provides a single assay which in principle can merge HTS and high content screening (HCS) data acquisition. The data acquisition impact on throughput of an assay can be minimized by acquiring a substantially reduced number of data points, for example, reduced by a factor of about 10 to about 100 or more. The method permits multiple receptor-coupled molecular pathways to be simultaneously interrogated. The method provides a label-free cell-based compound and pathway sensitive assay methodology. The method avoids fluorescent, luminescent, radioisotope, or like labels in live-cells that can cause false positive results in screening assays. The method provides a label-free assay cell-based methodology that can use non-engineered cell lines and primary cells, to provide results having a more meaningful physiological response.

DEFINITIONS

"Hit compound" classically refers to a compound that generates a positive response in a biological assay by exceeding a threshold value determined by positive and negative control compounds.

"Non-hit compound" classically refers to a compound that fails to generate a positive response in a biological assay because it does not exceed a threshold value determined by positive and negative control compounds.

"Profile" classically refers to the shape (or appearance) of a biological response when data is continuously acquired and plotted over a fixed time course.

"HCS" or "high content screening" and like terms classically refers to, for example, a technology that combines automated fluorescence microscopy with highly sophisticated image analysis software to provide a detailed analysis of cellular responses to chemical entities.

In the present disclosure:

"Kinetic profile" refers to the profile that is measured on a label-free system following the administration of a chemical compound to a cell. Activation of a GPCR by a compound generates a kinetic profile that is characteristic of the GPCR pathway being activated, i.e., the profile is pathway-specific. Active GPCR profiles can be measured above a detection threshold, for example, above about several hundred to about several thousand copies of the target receptor, such as above about 50 to about 100 femto-mole per milligram of receptor.

"Profiling" refers to a process in which the kinetic profile of multiple compounds (hit or non-hit) can be measured simultaneously in a high-throughput format, using a small number of data points.

"Plotting the delta response" refers to the difference in response (measured in picometers of wavelength shift in optical label-free systems) between data points measured in HTS. For example, if point 1 was 60 pm and point 2 was 100 pm then the delta response for point 2 minus point 1 is the difference 100 pm–60 pm=40 pm.

"Positive and negative controls" refers to the compounds and buffer solution, respectively, used to generate a kinetic profile for a GPCR receptor that will define the limits of the threshold.

"Threshold" refers to a region or space defined by positive and negative controls which space contains only non-hit compounds.

"Hit compound" refers to a compound that is outside the threshold. A hit compound can be, for example, a biologically or pharmacologically active entity, such as an agonist, an inverse agonist, an antagonist, or like entity, or a combination thereof.

"Pathway-specific" refers to the molecular pathway that is activated when a target receptor is engaged by a hit compound, and the ability to assign a label-free kinetic response profile to a specific pathway.

"High throughput" or like terms refer to a method, often utilizing highly automated robotic systems, to test or evaluate a large number of chemical entities for a defined biological response.

"Relational table," "look-up table," "relational chart," or like terms refer to the series of steps or procedures use to classify the response profile of a chemical entity in a high-throughput screen, i.e., an embedded algorithm.

"Identification," "identifying," or like terms refer to identifying hit compounds from non-hit compounds based upon the assignment of a threshold value determined by positive and negative control compounds "Selection," "selecting," refers to identifying the hit compounds that exceed the threshold value in a high-throughput screen.

"Screen," "screening," or like terms refers to, for example, a systematic survey of one or more compounds or drug candidates or biologicals (e.g., RNAi, antibody) to examine their pharmacological activities interacting with or acting on a particular target, a cell type, or a cell system. Pharmacological or biological activity is an expression describing the beneficial or adverse effects of a drug or other substance on living matter. Aspects of the disclosure are particularly useful in biosensor-based high throughput screening (HTS) and high-information content screening applications.

"HTS" or "high throughput screening" and like terms refers to, for example, a process in which large numbers of chemical compounds are tested for biological activity either by direct binding to a target molecule or via activation/inhibition of signaling pathways in whole cells.

"High-information content screening," (HICS) or and like terms as used in the disclosure refer to, for example, a method in which GPCR pathway-specific information can be obtained for compounds having, for example, 3 or 4 data points acquired using label-free HTS methods.

"Assay," "assaying" or like terms refers to an analysis to determine, for example, the presence, absence, quantity, extent, kinetics, dynamics, or type of a biomolecule's or a cell's optical or bioimpedance response, upon stimulation with an exogenous stimuli, such as a ligand candidate compound.

"Attached," "attach," or like terms refer to any interaction between two components or compounds. The type of interaction that can be formed will vary depending upon, for example, the starting components or compounds that are selected and the interaction conditions. Examples of attachments described herein include, for example, covalent, electrostatic, ionic, hydrogen, or hydrophobic bonding. "Attach," "attachment," "adhere," "adhered," "adherent," "immobilized," or like terms generally refer to immobilizing or fixing, for example, a cell, an antibody, a ligand candidate compound, and like entities, to a surface, such as by physical absorption, chemical bonding, and like processes, or combinations thereof. A biosensor surface can be modified, such as having a surface coating, an anchoring or tie material, a compatibilizer (e.g., fibronectin, collagen, lamin, gelatin, polylysine, etc.), or like modifications, and combinations thereof, that can promote, for example, receptivity of the biosensor surface towards particular molecular or cellular entities, such as in cellular binding, protein binding, and ligand detection.

"Contact" or "contacting" or like terms refer to, for example, an instance of exposure by an intimate physical encounter or touching of at least one substance to another substance.

"Target" or like terms refer to a cell, a protein, or like substance selected for immobilization. A target can be, for example, a receptor, a phosphatase, a kinase, an enzyme, a lipoprotein, a DNA, an RNA, and like entities including whole cells having a surface protein, and synthetic or genetically engineered proteins. A receptor can be, for example, a G protein-coupled receptor (GPCR), a receptor tyrosine kinase (RTK), a transporter, an ion-channel, an integrin receptor, a sodium/proton exchanger, and like entities. A kinase can be, for example, protein kinase A, protein kinase C, mitogen-activated protein (MAP) kinases, an extra-cellular signal-regulated kinases, Src, Rho kinase, focal adhesion kinase, and like entities. An enzyme can be, for example, a membrane-bound adenylyl cyclase, a soluble adenylyl cyclase, a protease, and like entities. A "target receptor" refers to any receptor that on binding a hit compound will have a unique and distinguishable profile.

"Biosensor" or like term refers to an article, that in combination with appropriate apparatus, can detect a desired analyte. A biosensor can combine a biological component with a physicochemical detector component. A biosensor can typically consist of three parts: a biological component or element (such as tissue, microorganism, pathogen, cells, cell component, a receptor, and like entities, or combinations thereof), a detector element (operating in a physicochemical way such as optical, piezoelectric, electrochemical, thermometric, magnetic, or like manner), and a transducer associated with both components. In embodiments, the biosensor can convert a molecular recognition, molecular interaction, molecular stimulation, or like event occurring in a surface bound cell component or cell, such as a protein or receptor, into a detectable and quantifiable signal. A biosensor as used herein can include liquid handling systems which are static, dynamic, or a combination thereof. In embodiments of the disclosure, one or more biosensor can be incorporated into a micro-article. Biosensors are useful tools and some exemplary uses and configurations are disclosed, for example, in PCT Application No. PCT/US2006/013539 (Pub. No. WO 2006/108183), published Dec. 10, 2006, to Fang, Y., et al., entitled "Label-Free Biosensors and Cells," and U.S. Pat. No. 7,175,980. Biosensor-based cell assays having penetration depths, detection zones, or sensing volumes have been described, see for example, Fang, Y., et al. "Resonant waveguide grating biosensor for living cell sensing," *Biophys. J.*, 91, 1925-1940 (2006). Microfluidic articles are also useful tools and some exemplary uses, configurations, and methods of manufacture are disclosed, for example, in U.S. Pat. Nos. 6,677,131, and 7,007,709. U.S. Patent Publication 20070141231 and U.S. Pat. No. 7,175,980, disclose a microplate assembly and method. The compositions, articles, and methods of the disclosure are particularly well suited for biosensors based on label-independent detection (LID), such as for example an Epic® system or those based on surface plasmon resonance (SPR). The compositions, articles, and methods of the disclosure are also compatible with Dual Polarized Intereferometry (DPI), which is another type of LID sensor. In embodiments, the biosensor system can comprise, for example, a swept wavelength optical interrogation imaging system for a resonant waveguide grating biosensor, an angular interrogation system for a resonant waveguide grating biosensor, a spatially scanned wavelength interrogation system, surface plasmon resonance system, surface plasmon resonance imaging, or a combination thereof.

"Protein" and like terms refers to the molecular target or like entity for entrapping, and can include, for example, a peptide, a polypeptide, a glycoprotein, a lipoprotein, a receptor, a receptor component, an antibody, and like natural or synthetic molecules, or mixtures thereof. "Protein" can include an individual protein molecule, a protein molecule in admixture, in association, in complexation, or like relations with other molecular or biological entities, including for example, whole cells, or subunits or portions thereof.

"Fibronectin coated plate" refers to a microwell biosensor plate having a surface treated with biologically active peptide, such as fibronectin or similar peptide material for promoting attachment of cells to a tissue culture substrate, which peptide has cell-attaching activity, see for example, now expired U.S. Pat. No. 4,517,686.

"EMA" generally refers to an exemplary ethylene-maleic anhydride (EMA) copolymer, or any derivative thereof, that can be used as a surface coating for culturing cells and for accomplishing optical waveguide measurements.

Other suitable surface coating can include, for example, collagen, gelatin, poly-D-lysine, and like coating compositions and mixtures thereof. The coating composition can be used as a thin film, for example, on certain Epic® biosensor well-plate products commercially available from Corning, Inc.

In embodiments, the coating of the coated biosensor can have "reactive groups" and "ionizable groups" and which groups refer to moieties that can chemically react and moieties than can ionize, respectively, and as defined in commonly owned, copending U.S. Ser. No. 12/273,147, filed Nov. 18, 2008, and commonly owned and assigned copending U.S. application Ser. No. 11/973,832, filed Oct. 10, 2007. In embodiments, certain reactive groups, such as s-NHS derivatives, can be a reactive group and an ionizable group. Another suitable surface coating is disclosed in commonly owned, copending U.S. Ser. No. 11/448,486, filed Jun. 7, 2006.

A "carboxy polymer surface," "surface bound carboxylate surface," or like terms refer to a surface bound polymer containing carboxylic acid functional groups or like carboxy functional groups, such as maleic anhydride groups. The polymer of the "carboxy polymer surface," can be, for example, an ethylene-maleic anhydride (EMA) polymer according to T. Pompe (Pompe, et. al, "Functional Films of Maleic Anhydride Copolymers under Physiological Conditions," *Macromol. Biosci.*, 2005, 5, 890-895). The polymer can be, for example, a polyacrylic acid polymer, or copolymer containing acrylic acid monomers. The polymer can be, for example, a carboxylated polysaccharide or like materials as disclosed, for example, in U.S. Pat. Nos. 5,242,828 and 5,436,161.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compositions or formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to cells, to a target compound or drug candidate, to an assay, to method of using the assay to screen compounds, and to articles, devices, or any apparatus of the disclosure, and can include the components or steps listed in the claim, plus other components or steps that do not materially affect the basic and novel properties of the articles, apparatus, or methods of making and use of the disclosure, such as particular reactants, particular additives or ingredients, a particular agents, a particular surface modifier or condition, or like structure, material, or process variable selected. Items that may materially affect the basic properties of the components or steps of the disclosure or that may impart undesirable characteristics to aspects of the disclosure include, for example, having to include a photo-active label or like label with the targeted pathway, protein, or ligand analyte, or restricting the assay to a single pathway. In embodiments, the disclosure provides an apparatus and process for analyzing one or more receptor pathways in live-cells.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, reactants, compounds, ligands, biologicals, times, temperatures, and like aspects, and ranges thereof, are for illustration only; they do not exclude other defined values or other values within defined ranges. The compositions and methods of the disclosure include those having any value or any combination of the values, specific values, more specific values, and preferred values described herein.

In embodiments, the issue of time-intensive data acquisition and processing in high-information content screening and the limited biological information provided by high-throughput screening can be overcome by, for example, limiting or minimizing data acquisition to pre-selected portions of pre-determined profiles of a targeted receptor and its signaling pathways. The measured receptor response(s) to each ligand candidate can be further processed in accordance with the disclosed method to provide a systematic characterization of each response. The characterization can be used to readily identify and differentiate hit compounds from, for example, non-hit compounds or weak hit compounds.

In embodiments, the disclosure provides a method for hit compound identification in a high throughput, label-free biosensor cellular assay, the method comprising:

generating at least one pathway-specific kinetic profile for a target receptor;

generating a relational table, which table incorporates each kinetic profile;

determining a delta response based on the relational table for each of a plurality of candidate compounds screened against the target receptor; and identifying hit compounds based upon the separation of the delta response from the threshold.

The threshold can be, for example, the upper and lower limits or range of the response region for positive and negative control compounds. The "separation" can be, for example, a data point which lies outside an upper threshold value or a lower threshold value. A data point outside an upper threshold value represent a $G_s$ hit compound, and a data point outside a lower threshold value represent a $G_q/G_i$ hit compound. A threshold value can be, for example, 50% of the positive control value.

There are numerous ways to determine a threshold value or limit. In one example, the standard deviation and the mean response of the negative controls was used. A formula for an upper threshold value can be, for example:

Mean+(5*std. dev. of negative control).

A formula for a corresponding lower threshold value can be, for example:

Mean−(5*std. dev. of negative control).

In embodiments, another method that can be used to determine a threshold value is a value that is 50%, or some other arbitrary but useful percentage (%) value, of a positive control value. In embodiments, numerous other similar methods can be devised and used to determine a threshold value or range of threshold values.

In embodiments, the method can further comprise plotting the delta response determined for each compound screened against the target receptor.

In embodiments, generating at least one pathway-specific kinetic profile for a target receptor can be, for example, accomplished using a live-cell. The live-cell can be, for example, at least one of: a eukaryote, a prokaryote, a hybrid, a synthetic construct, or a combination thereof. A suitable live-cell can be any cell including, for example, an organ or tissue cell such as a liver cell, a lung cell, a brain cell, a skin cell, an islet (i.e., insulin-producing) cell, a mast cell, and like organ or tissue like cells, or a combination thereof. Other suitable cells can include, for example, a diseased-state cell, such as a tumor cell, an infected cell, a cancerous cell, and like cells, or a combination thereof. Still other suitable cells can include, for example, a normal cell, a stem cell, a T-cell, a helper T-cell, a B-cell, a transmitter-producing cell, a monocyte, an engineered cell, hybridomas, or mixtures thereof. The live-cell can be, for example, a native cell comprising an HEK293 cell or cells.

In embodiments, the target receptor can be, for example, a GPCR. Other suitable target receptor can be any target including, for example, an ion-channel receptor, a tyrosine kinase receptor, and like receptors or targets, or a combination thereof.

In embodiments, the candidate compound can be, for example, an agonist (full or partial), an antagonist, an inverse agonist, a positive control, a negative control, or a combination thereof.

In embodiments, a kinetic profile can be accomplished in HTS format, for example, in about 8 hrs with from 2 to about 3 data points compared to about 80 hrs and greater than about 50 data points. In embodiments, an HTS format can accomplish, for example, about 30,000 wells of data in about 8 hrs compared to about 80 hours, such as if data is read continually for about 40 mins.

In embodiments, the disclosure provides a method for classifying active GPCR receptor responses, the method comprising, for example:

generating a pathway-specific kinetic profile for a GPCR receptor;

generating a relational table that integrates each kinetic profile;

determining a delta response from the relational table for each of a plurality of candidate compounds screened against the GPCR receptor; and classifying the delta response for each candidate compound as a $G_s$ hit compound, a $G_q/G_i$ hit compound, or a non-hit compound.

Label-dependent technologies depend on prior knowledge of the pathway. Thus, if one studies a $G_s$-coupled receptor, one selects a methodology that enables $G_s$ responses to be measured. Other GPCR receptor responses can be blind or unobserved. Other label-free products and systems can measure different receptor responses but none are believed to offer a method to measure responses in a HTS format. The classifying can be accomplished with cell types that endogenously express the target GPCRs, that is, cells that have not been engineered. In embodiments of the present disclosure, the method for classifying active GPCR receptor responses can be accomplished in a single assay.

In embodiments, the disclosure provides a method for GPCR agonist hit identification in a high throughput, label-free live-cell biosensor assay, the method comprising, for example:

contacting a live-cell having a GPCR with a first compound to determine a first difference response ($\Delta R_1$) according to:

$$\Delta R_1 = R_3 - R_2$$

where $R_3$ is a third time domain response, and $R_2$ is a second time domain response to the first compound;

determining a second difference response ($\Delta R_2$) according to:

$$\Delta R_2 = R_2 - R_1$$

where $R_2$ the second time domain response, and $R_1$ is a first time domain response to the first compound; and determining a delta response ($\Delta R_3$) according to:

$$\Delta R_3 = \Delta R_1 - \Delta R_2$$

The method can further comprise, for example, contacting the GPCR with a plurality of compounds to determine their respective difference responses and delta responses.

The method can further comprise, for example, plotting the delta response for each compound then selecting hit compounds from non-hit compounds, based upon, for example, the separation of the delta response for the hit compounds from the delta response for the non-hit compounds, that is the control compounds and the negative controls.

In embodiments, if the compound is an agonist, then the first time domain response $R_1$ can be, for example, obtained at from 0 to about 2 minutes, the second time domain response $R_2$ can be, for example, obtained at from about 2 to about 20 minutes, and the third time domain response $R_3$ can be, for example, obtained at from about 20 to about 60 minutes.

In embodiments:

if the compound is a hit for a $G_q$ receptor, a $G_i$ receptor, or both receptors, then:
$\Delta R_1$ is 0 or negative,
$\Delta R_2$ is positive, and
$\Delta R_3$ is negative;
if the compound is a hit for a $G_s$ receptor, then:
$\Delta R_1$ is positive,
$\Delta R_2$ is 0 or negative, and
$\Delta R_3$ is positive; and
if the compound is a non-hit, then:
$\Delta R_1$ is 0,
$\Delta R_2$ is 0, and
$\Delta R_3$ is 0.

In embodiments:

if the compound is a hit for either or both a $G_q$ or a $G_i$ receptor, then $\Delta R_3$ is negative;
if the compound is a hit for a $G_s$ receptor, then $\Delta R_3$ is positive; or
if the compound is a non-hit, then $\Delta R_3$ is 0.

In embodiments, if the compound is an inverse agonist then the method can further comprise determining an additional profile where:
$\Delta R_1$ is 0;
$\Delta R_2$ is negative; and
$\Delta R_3$ is positive.

In embodiments, the disclosure provides a method for GPCR antagonist hit identification in a high through-put, label-free biosensor cellular assay, the method comprising the aforementioned method, that is, generating at least one pathway-specific kinetic profile for a target receptor;

generating a relational table, which table incorporates each kinetic profile;

determining a delta response based on the relational table for each of a plurality of candidate compounds screened against the target receptor; and identifying one or more hit compound based upon the separation of the delta response from the threshold, and further comprising:

adding a single second compound (i.e., a known agonist compound) to each assay well after contacting the receptor with the first compound (i.e., an antagonist candidate compound) to create an additional response point $R_4$ measured at about 10 mins ($G_q/G_i$ agonist) or about 60 mins ($G_s$ agonist) after $R_3$ and calculating a delta response ($\Delta R_{1antagonist}$) of zero according to the formula:

$$\Delta R_{1antagonist} = R_4 - R_3.$$

In embodiments, the disclosure provides a method for simultaneously identifying any "hit" compound and associated signal pathway information while evaluating a plurality of potential compounds in a high throughput and high information content screen operation. A profiling algorithm enables compound hits to be readily identified in conjunction with signal pathway information.

Referring to the Figures, FIGS. 1A to D show representative optical profiles for each of the major classes of GPCR. Optical responses were measured in HEK293 cells for 40 minutes to obtain the characteristic profile of compounds known to activate receptors which are: A) $G_q$-coupled; B) $G_i$-coupled; C) $G_s$-coupled; and D) not expressed in, for example, HEK293 cells. Data points 1 (2 mins), 2 (10 mins) and 3 (40 mins) were selected for HTS profiling. For example, a portion (320 compounds) of the LOPAC compound library (LOPAC subsets available from Sigma-Aldrich) was first screened on HEK293 cells to determine the optical profiles for known GPCR agonists. The LOPAC library contains 1,280 well-characterized compounds whose targets include GPCRs known to be expressed on HEK293 cells. The LOPAC library is a standard tool used to validate new High Throughput Screening assays. Other libraries or like collections of compounds having known or unknown activity can be used in the assay. Optical biosensor profiles for each of the major classes of GPCRs are shown in FIG. 1, where:

FIG. 1A shows a $G_q$ profile using methylcholine chloride;

FIG. 1B shows a $G_i$ profile using (2S)—N-6-[2-endo-Norbornyl]adenosine (i.e., ENBA);

FIG. 1C shows a $G_s$ profile using 2-(1-Hexyn-1-yl)adenosine-5'-N-ethyluronamide, 2-Hexynyl-5'-ethylcarboxamidoadenosine (i.e., HE-NECA); and FIG. 1D shows a non-hit profile using cyclothiazide. Note that the FIG. 1D profile is also expected for or representative of a buffer-only control.

For each compound screened, an initial two (2) minute baseline was measured, followed by compound addition and a continuous measurement of the optical response for 40 minutes. By selecting just three (3) data points (arrows indicating points 1, 2, and 3 in FIGS. 1A-D), for example, at 2 mins, 10 mins, and 40 mins, GPCR responses can be designated into three distinct classes or categories. Compounds that activate $G_q$ or $G_i$-coupled receptors represent one class of responses and have a characteristic rapid positive signal peak which then decreases or decays and finally plateaus at a response level between the peak and the baseline (see FIGS. 1A and 1B). A second class of responses is for receptors which are $G_s$-coupled where an initial signal decrease is followed by a steady signal increase for the remainder of the measured time (FIG. 1C). A third class of responses is for compounds that fail to activate a receptor and result in an essentially flat response from baseline to the final measurement at, for example, 40 minutes (FIG. 1D).

Table 1 provides an outline of the procedure use to identify hits from HTS data and categorize each according to the type of GPCR activated. The final characteristic response ($\Delta R_3$) for each type of hit is listed in step 3 for the respective GPCR pathway. Using the respective data points (1, 2, and 3) shown in the respective FIGS. 1A to 1D, a problem-solving procedure was developed that categorized or classified each characteristic response or profile (see Table 1) that was identified into a single data plot (see FIG. 2). In Step 1 the response value at point 2 ($R_2$) was subtracted from the response value at point 3 ($R_3$) to give a step difference value ($R_3-R_2=\Delta R_1$), referred to as the delta response ($\Delta R$ measured in picometers (pm)). Similarly, the delta response in Step 2 was determined by subtracting the response value at point 1 ($R_1$) from the response value at point 2 ($R_2$) to give a step difference value ($R_2-R_1=\Delta R_2$). These values were then used in Step 3 to determine the delta response for Step 2 subtracted from Step 1 ($\Delta R_3=\Delta R_1-\Delta R_2$).

TABLE 1

Procedural Summary for HTS Profiling of GPCR Pathways.

| Step | Delta Response ($\Delta R_n$) | $G_q/G_i$ Hit Response | $G_s$ Hit Response | Non-Hit Response |
|---|---|---|---|---|
| 1 | $\Delta R_1 = R_3 - R_2$ i.e., point 3 less point 2 | 0 or negative | positive | 0 |
| 2 | $\Delta R_2 = R_2 - R_1$ i.e., point 2 less point 1 | positive | 0 or negative | 0 |
| 3 | $\Delta R_3 = \Delta R_1 - \Delta R_2$ i.e., step 1 response less step 2 response | negative | positive | 0 |

Table 1 summarizes the expected outcome for the three categories of GPCR responses at each step of the problem solving procedure. For example, point 3 of the $G_s$ profile is greater in value than point 2 (FIG. 1C); therefore the delta response at Step 1 will be a positive value. In Step 2, the response values for point 1 and point 2 are subtracted, i.e., point 2 less point 1, or $\Delta R_2=R_2-R_1$.

In the example shown, point 2 is selected at 10 minutes. All of these data points are prescribed by the control profiles; for HEK cells the following times were selected: 2 mins (pt 1), 10 mins (pt 2), and 40 mins (pt 3). The peak of the $G_q/G_i$ response occurred at 10 mins, whereas the minima point of the $G_s$ response occurred several minutes later. Since a single time point can be used to maintain throughput, 10 mins was selected. However, similar time values, such as 11 or 12 mins, including intermediate values and ranges, can be selected. A single time point can be selected for step 2 which captures the significant features of the profiles (i.e., close to the maximum of $G_q/G_i$ and close to the minimum of $G_s$). This time point can be earlier or later for different cell lines. Responses in HEK cells are likely not representative of all cell types. Instead, control compounds for each pathway can be used in a preliminary evaluation with any new cell type, which allows an operator to select the time points ("pt") for the new cell type. At step 2 the response values for pt 1 and pt 2 will be very similar resulting in a delta response that is either zero or a small negative number. Subtraction of the small value of Step 2 from the large value in Step 1 results in a final delta response value in Step 3 that has a positive value. Hence, compounds that activate $G_s$-coupled receptors will have positive values in Step 3 of the method. In contrast, $G_q/G_i$-coupled responses will typically have a negative response value in Step 1. Exceptions to a negative response value in Step 1 are, for example, responses which plateau after the initial peak, which would have a response value close to zero. $G_q/G_i$ coupled responses will typically have a positive value at Step 2. The delta response for $G_q/G_i$ active compounds in Step 3, i.e., $\Delta R_3=\Delta R_1-\Delta R_2$, is a negative value. Compounds which fail to activate a receptor (Non-Hits) have a zero response value at Steps 1 and 2 of the method and consequently, the delta response value in Step 3 is also zero. Plotting the data from Step 3 enables the classes of responses to be easily identified in a single graphic display (FIG. 2).

The present disclosure provides a method that can, for example, analyze GPCR profiles or like profiles, in a single assay and which assay is not limited to a single pathway.

Figure 1:
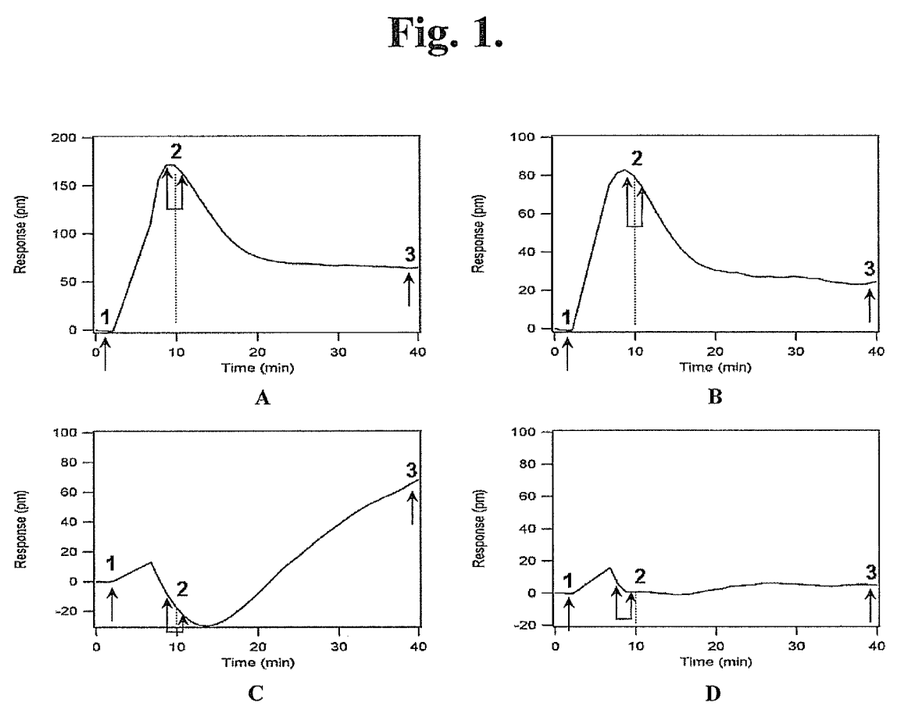
FIG. 1 shows representative optical profiles for each of the major classes of GPCR.
Figure 2:
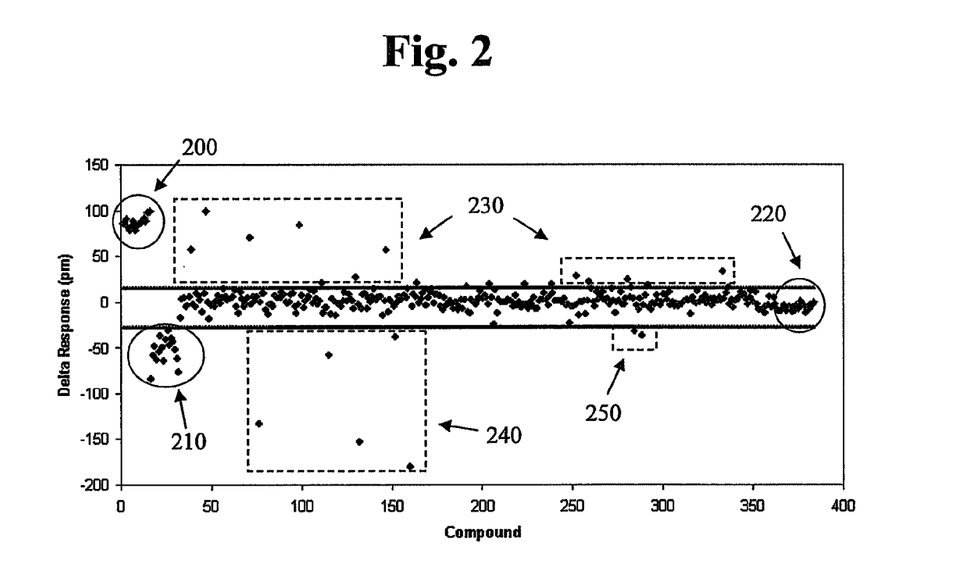
FIG. 2 illustrates an exemplary HTS profiling of GPCR pathways in HEK293 cells using the LOPAC library.

FIG. 2 plots the delta response ($\Delta R$) values for a high throughput screening analysis of the entire LOPAC library of compound. Distinct control clusters and hit out-lier patterns that emerge from applying the method include, for example, $G_s$ control compound(s) (200), $G_q/G_i$ control compound(s) (210), negative control compound(s) (220), $G_s$ agonist hit compound(s) (230), $G_q/G_i$ agonist hit compound(s) (240), and weak $G_q/G_i$ agonist compounds (250).

FIG. 2 illustrates an exemplary HTS profiling of GPCR pathways in HEK293 cells using the LOPAC library. LOPAC Plate #3 compound responses were measured in HTS with a baseline read at 2 mins, followed by endpoint reads at 10 mins and 40 mins. Data were analyzed using the profiling algorithm described in the text. The upper line at 15 pm is the threshold for $G_s$ agonists, while the lower line at −25 pm is the threshold value for $G_q/G_i$ agonists. All of the compounds with responses between these threshold lines are non-hits. Controls for the experiment are indicated with circles, and candidate hits in each category are identified by the dashed rectangles.

The disclosed method complements and further advances our previous discoveries relating to methodologies for GPCR cell assays using waveguide-grating biosensors (see commonly owned and assigned U.S. Ser. No. 11/100,262, filed Apr. 5, 2005, and divisional application U.S. Ser. No. 12/469,054, filed May 20, 2009).

The disclosed method can be applied to signaling pathways other than GPCRs.

Other suitable classes of receptors include, for example, tyrosine kinase receptors (see Fang, Y., et. al., "Characteristics of Dynamic Mass Redistribution of Epidermal Growth Factor Receptor Signaling in Living Cells Measured with Label-Free Optical Biosensors," Anal Chem, 2005, 77, 5720-5725), and ion channel receptors also have unique optical profiles. For example, by altering the timing selection of the data points acquired after compound addition to capture the important characteristics of these profiles, the disclosed receptor pathway profiling approach could be adapted to screen and identify hit compounds activating these receptor pathways. Alternatively, measurement of one additional data point, for example, either between 10 minutes and 40 minutes, or after 40 minutes, can permit a method to be accomplished that evaluates multiple receptor families in a single screening trial.

EXAMPLES

The following examples serve to more fully describe the manner of using the above-described disclosure, as well as to further set forth the best modes contemplated for carrying out various aspects of the disclosure. It is understood that these examples do not limit the scope of this disclosure, but rather are presented for illustrative purposes.

The working examples further describe how to make and use the methods of the disclosure.

Materials and Methods a) Cell Culture

Stock subcultures of HEK293 cells were grown in Dulbecco's Modified Eagle's Medium containing 10% heat-inactivated Fetal Bovine Serum, 2 mM L-Glutamine, and 100 microg/mL Penicillin-Streptomycin on standard TCT growth surfaces for 3 days (at about 70-80% confluence) in a 37° C./5% $CO_2$ incubator. The cell stocks were harvested using enzymatic removal with 0.25% Trypsin-Versene solution. Harvested cells were washed once in complete medium and counted. Cells were then seeded into a single Epic® 384-well Fibronectin-Coated Cell Assay Microplate using a Multidrop Combi cell culture dispensing system at a cell density of about 18K cells/well. The seeded plate was allowed to remain at room temperature for 30 minutes to allow the cells to uniformly settle on the growth surface of the well and then incubated prior to beginning the assay. The average incubation was about 18 to 22 hours in a 37° C./5% $CO_2$ incubator.

b) Plate Washing

At about 18 to 22 hours post-seeding, the assay plate was removed and visually inspected using a microscope to ensure that the cells had formed a confluent monolayer. The plate was then washed three times with 1× Hank's Balanced Salt Solution containing 20 mM HEPES and 0.6% DMSO (i.e., "assay buffer") using the BioTek ELX405CW Plate Washer. 30 microliters of assay buffer remained in each well of the plate after washing. The plate was then stored in the Cytomat Hotel of the Epic® HTS Workstation for 1 hour before the assay to permit the cells to recover from the washing procedure.

c) Compound Source Plate

A Library of Pharmacologically Active Compounds (LOPAC) Plate #3 was prepared at 4 microM (4× assay concentration) in a Corning 384-well polypropylene plate via a 2-step dilution process on the Evolution P3 (Perkin Elmer). 1 microliter of the 666.67 microM primary stock in 100% DMSO was first diluted in 32.3 microliters of HBSS/20 mM HEPES without DMSO (dilution buffer) to give an intermediate dilution of 20 microM compound in 3% DMSO. 4 microliters of the intermediate dilution was then transferred to 16 microliters of dilution buffer to give the 4× assay concentration of 4 microM compound in 0.6% DMSO. The final source plate was stored on the Cybi® Stacker (cybio-ag.com) of the Epic® HTS Workstation (corning.com/lifesciences) for immediate use.

d) Epic® Cell-Based Assay

After the 1 hour assay plate incubation step, the assay was run using the CyBio Scheduler software to accomplish the following procedure. First, the assay plate was transferred into the Epic® Reader and stored on the carousel for 2 minutes, after which, a single baseline data point was measured. Second, the assay plate was exported from the Reader for addition of the LOPAC compounds from the source plate using a CyBio 384-well pipettor for the addition of 10 microliters of compound or buffer from the source plate into the correct wells of the assay plate. Following compound addition, the assay plate was returned to the Reader and stored on the carousel for 7.5 minutes (about 10 minutes total assay time) before measuring an intermediate data point. Lastly, the assay plate was incubated on the carousel for a further 30 minutes (about 40 minutes total assay time), and a final data point was measured.

e) Profiling Algorithm

All data was analyzed using the Epic® Microplate Analyzer v2.0 and Microsoft Excel, according to the algorithm summarized in Table 1. In step 1, the Epic® Microplate Analyzer was used to calculate the delta response for the final data point (point 3) minus the intermediate data point (point 2), and the data transferred to a 384-well plot in Microsoft Excel®. This procedure was then repeated in step 2 to calculate the delta response for the intermediate data point (point 2) minus the baseline data point (point 1). To obtain a final delta response for each compound in step 3, Microsoft Excel® was used to subtract step 2 values from step 1 values, and the data set was plotted as shown in FIG. 2.

Example 1 (Actual)

Hit Characterization and Identification

To demonstrate the utility of the method to identify known or new hits, and to assign them to the correct pathway, LOPAC Plate #3 was tested on HEK293 cells using an HTS format for data acquisition. Compound responses were measured only at selected points 1, 2, and 3 described above and then analyzed with the algorithm using templates in Microsoft Excel®. The resulting data set is shown in FIG. 2. Positive control compounds were tested at the same screening concentration (1 microM) as the LOPAC compounds. The $G_s$-coupled control was isoproterenol, which compound is a known agonist for β-adrenergic receptors. The $G_q/G_i$ coupled control was carbachol, which compound targets the muscarinic M1 receptor. From inspection of the plotted points in FIG. 2, the upper and lower threshold limits were calculated using the value for five (5) times the standard deviation (σ) of the negative control (i.e., assay buffer only). The upper and lower lines therefore represent the mean buffer response zone of +5σ or −5σ, respectively, i.e., about +15 to about −25 response units. Using these thresholds it is clear that the majority of the library compounds fail to elicit any kind of response in the assay, as expected for this LOPAC plate. In contrast, each of the positive control wells (200 and 210) was correctly identified. A small number of hits were identified as either $G_g/G_i$ agonists or $G_s$ agonists and are contained in the dashed rectangle regions in FIG. 2. Each of these hits was independently shown to specifically target receptors that are activated in accordance with the method's prediction. That is, the $G_s$ agonists all target $G_s$-coupled receptors and the $G_q/G_i$ agonists all target $G_g/G_i$-coupled receptors. Consequently, none of these hits was a false positive. Two potential $G_q/G_i$ agonist compounds (Pilocarpine nitrate and (+)-Pilocarpine hydrochloride) (250) were not identified as hits in this experiment but work in various experimental systems has shown that these compounds are only weak partial agonists (see for example, Rhee, J. C., et. al., "Muscarinic receptors controlling the carbachol-activated nonselective cationic current in guinea pig gastric smooth muscle cells.," *Jpn J Pharmacol*, 2000, 82, 331-337). Other than these very weak agonists, there were no apparent false negative responses in this experiment.

Example 2 (Actual)

Signal Pathway Results

To demonstrate signal pathway information while maintaining throughput capability, a three-point measurement selection was used rather than a two-point measurement selection used in many traditional HTS systems. To establish the impact of the additional data point measurement step on the throughput capability of the assay, simulations were accomplished with CyBi plate scheduling software that calculates the time required for a given number of plates to be processed according to the data acquisition method. A typical industry minimum performance standard for HTS is at least about 80 plates per day, so the time required for 80 plates to be processed with two (2) data points (baseline and 10 minutes, or baseline and 40 minutes) was compared with the time required for 80 plates processed with three (3) data points for the profiling algorithm. 80 plate simulations were accomplished using scheduling software and the total time to completion is shown in Table 2. As shown in Table 2, both simulations having two (2) data points require about 9 hours for completion. Acquisition of an additional data point for the disclosed three point HTS method increased the 80 plate simulation time by about three (3) hours, resulting in a total run time of about 12.4 hours, indicating that three-point method is compatible with typical HTS time requirements. In contrast, to screen 80-plates with full optical profiles (e.g., 53 data point selection) would require several days. Thus, the disclosed three point method approach provides considerable time savings and efficiency for hit compound screening.

TABLE 2

Comparative times for an 80-plate sampling rate simulation for 2-point, 3-point, and 53-point HTS.

| | 2 Data Points @ 2 and 10 mins | 2 Data Points @ 2 and 40 mins | 3 Data Points @ 2, 10 and 40 mins | 53 Data Points @ full 40 mins per point |
|---|---|---|---|---|
| Time required to run 80 plates | 9.1 hours | 9.4 hours | 12.4 hours | 79.8 hours |

Column 1 is an example of conventional HTS as shown in FIG. 1A for points 1 and 2.
Column 2 is an example of conventional HTS as shown in FIG. 1C for points 1 and 3.
Column 3 is an example of the disclosed method for points 1, 2, and 3.
Column 4 is an example of low throughput for points 1, 2, and 3.

Example 3 (Prophetic)

The disclosed profiling method can be used for other types of agonist hit identification and classification.

Inverse Agonists

Figure 3:
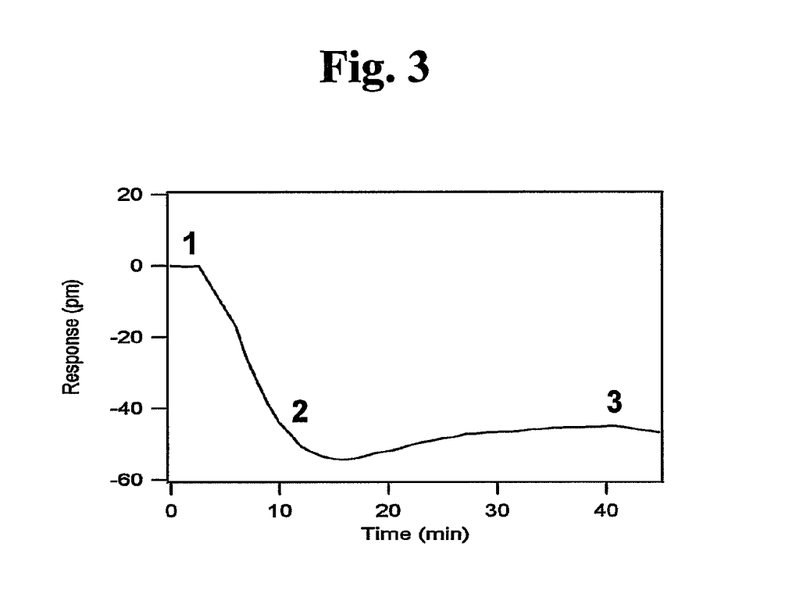
FIG. 3 illustrates an expected profile for an inverse agonist.

Compounds acting as inverse agonists on GPCRs have an optical profile that is different from the profile observed for $G_s$-coupled or $G_q/G_i$-coupled agonists. Using the disclosed algorithm, the inverse agonist compounds would result in a zero response in step 1 and a negative response in step 2. The delta response in step 3 would be positive, which is the same as a $G_s$ hit except that the responses in steps 1 and 2 would be distinct, e.g., $\Delta R_1=0$; $\Delta R_2$=negative; and $\Delta R_3$=positive, so it is straightforward to distinguish between an agonist and an inverse agonist type response. FIG. 3 provides an illustrative profile expected for an inverse agonist and the responses and procedure are summarized in relational Table 3.

TABLE 3

Procedural Summary for Inclusion of Inverse Agonist Hits During HTS Profiling of GPCR Pathways.

| Step | Delta Response $(\Delta R_n)$ | $G_q/G_i$ Hit Response | $G_s$ Hit Response | Inverse Agonist | Non-Hit Response |
|---|---|---|---|---|---|
| 1 | $\Delta R_1 = R_3 - R_2$ i.e., point 3 less point 2 | 0 or negative | positive | 0 | 0 |
| 2 | $\Delta R_2 = R_2 - R_1$ i.e., point 2 less point 1 | positive | 0 or negative | negative | 0 |
| 3 | $\Delta R_3 = \Delta R_1 - \Delta R_2$ i.e., step 1 response less step 2 response | negative | positive | positive | 0 |

Antagonists To identify antagonists, a second compound addition step is included after multiple agonists have been profiled using $R_1$, $R_2$ and $R_3$. In the second addition step, a single agonist compound is added to every well and a final data point ($R_4$) is measured, for example, either 10 mins ($G_q/G_i$ agonist) or 60 mins ($G_s$ agonist) after $R_3$. The additional data point $R_4$ can be used in the disclosed method and the antagonist relational table to calculate the delta response for $R_4$ minus point $R_3$ ($\Delta R_{1antagonist}=R_4-R_3$). The combination of $\Delta R_{1antagonist}$ (step 1) with $\Delta R_2$ and $\Delta R_3$ (steps 2 and 3) in the antagonist relational table enables antagonist compounds to be identified together with $G_q/G_i$ and $G_s$ agonists in a single assay.

Figure 4:
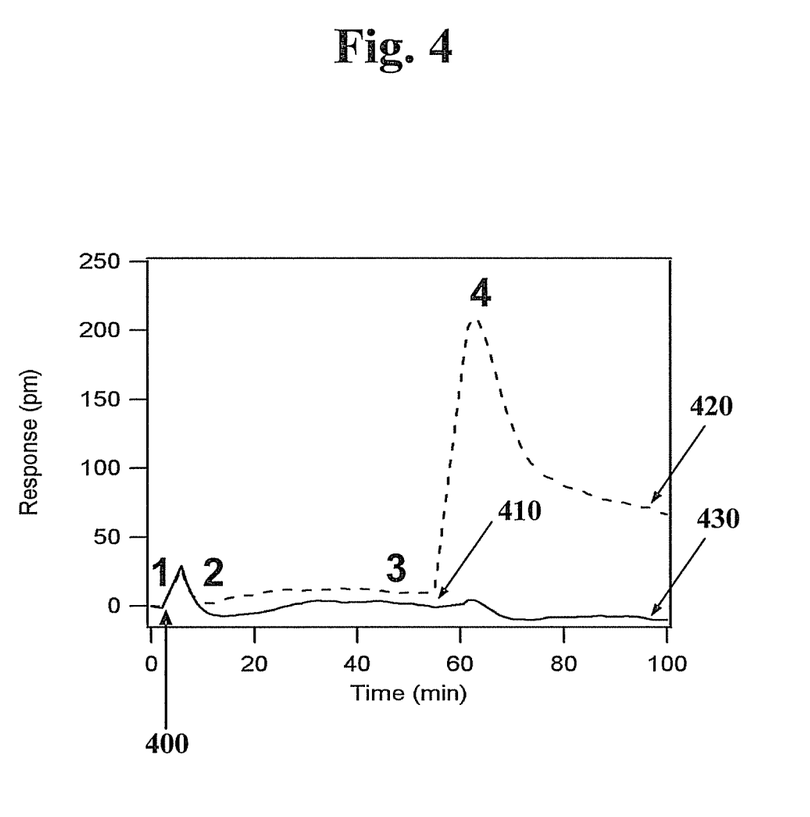
FIG. 4 illustrates an exemplary profile for an antagonist compared to a non-antagonist.

FIG. 4 provides illustrative profiles expected for an antagonist compound compared to a non-antagonist on a targeted receptor. The action of an antagonist candidate on the receptor as a first compound addition (400) before the addition of an agonist second compound (410) prevents or blocks any response from the added agonist compound and provides a profile that remains relatively flat and characteristic of an antagonist (430). If all the delta responses are zero using the disclosed method then the first compound added to the cells is an antagonist of the targeted receptor. However, if a profile shows a significant response upon addition of agonist second compound (410), then the first added antagonist candidate is not an antagonist compound but is instead a non-antagonist compound (420). Relational Table 4 provides the responses and procedures for antagonists.

TABLE 4

Procedural Summary for Inclusion of Antagonist Hits During HTS Profiling of GPCR Pathways.

| Step | Delta Response $(\Delta R_n)$ | $G_q/G_i$ Hit Response | $G_s$ Hit Response | Antagonist | Non-Hit Response |
|---|---|---|---|---|---|
| 1 | $\Delta R_1 = R_4 - R_3$ i.e., point 4 less point 3 | positive | positive | 0 | positive |
| 2 | $\Delta R_2 = R_3 - R_2$ i.e., point 3 less point 2 | 0 or negative | positive | 0 | 0 |
| 3 | $\Delta R_3 = R_2 - R_1$ i.e., point 2 less point 1 | positive | 0 or negative | 0 | 0 |

The disclosure has been described with reference to various specific embodiments and techniques. However, it should be understood that many variations and modifications are possible while remaining within the spirit and scope of the disclosure.

What is claimed is:
1. A method for hit compound identification in a high throughput, label-free biosensor cellular assay, the method comprising:

(a) generating at least one signaling pathway-specific kinetic profile for a target cell membrane receptor in a live-cell, wherein the at least one signaling pathway-specific kinetic profile for the target cell membrane receptor is obtained by:
  (i) providing an optical biosensor having a single type of live-cell immobilized on a surface of the biosensor, the biosensor being situated in a well of a microtiter plate, and the live-cell having a first and second target, wherein the first target is a cell membrane receptor, wherein the second target is a cellular protein, wherein the cellular protein is a member of the signaling pathway triggered by activation of the cell membrane receptor,
  (ii) separately stimulating the live-cell expressing target cell membrane receptor with a plurality of candidate compounds after the live-cell is attached to the surface of the biosensor;
  (iii) contacting the ligand candidate-treated live-cell with a mixture containing two markers; and
  (iv) determining the effect of the ligand candidate on the marker mixture-induced biosensor output;
(b) generating a relational table, which table incorporates each signaling pathway-specific kinetic profile for the plurality of candidate compounds;
(c) determining a delta response based on the relational table for each of the plurality of candidate compounds screened against the target cell membrane receptor; and
(d) identifying hit compounds from the plurality of candidate compounds based upon the separation of the delta response from a threshold.

2. The method of claim 1 wherein the threshold comprises the upper and lower limits of the response region for positive and negative control compounds.

3. The method of claim 1 wherein the separation comprises a data point outside an upper threshold value or a lower threshold value.

4. The method of claim 3 wherein the target cell membrane receptor is a G protein-coupled receptor (GPCR), wherein a data point outside an upper threshold value represents a $G_s$ hit compound, and a data point outside a lower threshold value represents a $G_q/G_i$ hit compound in the GPCR target cell membrane receptor.

5. The method of claim 2 wherein a threshold value is 50% of the positive control value.

6. The method of claim 1 further comprising plotting the delta response determined for each compound screened against the target cell membrane receptor.

7. The method of claim 1 wherein the live-cell comprises at least one of: a eukaryote, a prokaryote, a hybrid, a synthetic construct, or a combination thereof.

8. The method of claim 1 wherein the target cell membrane receptor comprises a G protein-coupled receptor (GPCR), a tyrosine kinase, an ion channel, or a combination thereof.

9. The method of claim 1 wherein the candidate compound comprises an agonist, an antagonist, an inverse agonist, a positive control, a negative control, or a combination thereof.

10. The method of claim 1 wherein the signaling pathway-specific kinetic profile is accomplished in high throughput screening (HTS) format in about 8 hours with from 2 to about 3 data points compared to a full signaling pathway-specific kinetic profile about 80 hours and greater than about 50 data points.

11. A method for classifying active G protein-coupled receptor (GPCR) responses, the method comprising:
  (a) generating at least one signaling pathway-specific kinetic profile for a target GPCR in a live-cell, wherein the at least one signaling pathway-specific kinetic profile for the target cell membrane receptor is obtained by:
    (i) providing an optical biosensor having a single type of live-cell immobilized on a surface of the biosensor, the biosensor being situated in a well of a microtiter plate, and the live-cell having a first and second target, wherein the first target is a GPCR, wherein the second target is a cellular protein, wherein the cellular protein is a member of the signaling pathway triggered by activation of the GPCR,
    (ii) separately stimulating the live-cell expressing target cell membrane receptor with a plurality of candidate compounds after the live-cell is attached to the surface of the biosensor;
    (iii) contacting the ligand candidate-treated live-cell with a mixture containing two markers; and
    (iv) determining the effect of the ligand candidate on the marker mixture-induced biosensor output;
  (b) generating a relational table that includes each signaling pathway-specific kinetic profile for the plurality of candidate compounds;
  (c) determining a delta response from the relational table for each of the plurality of candidate compounds screened against the GPCR; and
  (d) classifying the delta response for each of the plurality of candidate compounds as a Gs hit compound, a Gq/Gi hit compound, or a non-hit compound.

12. The method of claim 1, further comprising: wherein the candidate compound is an antagonist,
  adding a single second compound to each assay well after contacting with a first antagonist candidate compound to create an additional response point $R_4$ measured at from about 10 mins to about 60 mins after $R_3$, wherein $R_3$ is a third time domain response and calculating a $\Delta R_{1antagonist}$ delta response of zero according to the formula:

$$\Delta R_{1antagonist} = R_4 - R_3.$$

* * * * *